(12) United States Patent
Rizkalla

(10) Patent No.: US 6,858,560 B2
(45) Date of Patent: Feb. 22, 2005

US006858560B2

(54) ETHYLENE OXIDE CATALYST

(75) Inventor: Nabil Rizkalla, Rivevale, NJ (US)

(73) Assignee: Scientific Design Co., Inc., Little Ferry, NJ (US)

( * ) Notice: Subject to any disclaimer, the term of this patent is extended or adjusted under 35 U.S.C. 154(b) by 0 days.

(21) Appl. No.: 10/421,208

(22) Filed: Apr. 23, 2003

(65) Prior Publication Data

US 2004/0215026 A1 Oct. 28, 2004

(51) Int. Cl.$^7$ ............................................ B01J 21/02
(52) U.S. Cl. ...................... 502/202; 502/203; 502/216; 502/217; 502/218
(58) Field of Search ................................. 502/202, 203, 502/216, 217, 218

(56) References Cited

U.S. PATENT DOCUMENTS

| | | |
|---|---|---|
| 3,702,259 A | 11/1972 | Nielsen |
| 3,888,889 A | 6/1975 | Kolombos et al. |
| 3,962,136 A | 6/1976 | Nielsen et al. |
| 4,007,135 A | 2/1977 | Hayden et al. |
| 4,908,343 A | 3/1990 | Bhasin |
| 5,011,807 A | 4/1991 | Hayden et al. |
| 5,051,395 A | 9/1991 | Mitchell et al. |
| 5,057,481 A | 10/1991 | Bhasin |
| 5,100,824 A | 3/1992 | Vora |
| 5,102,848 A | 4/1992 | Soo et al. |
| 5,145,824 A | 9/1992 | Buffum et al. |
| 5,384,302 A | 1/1995 | Gerdes et al. |
| 5,486,628 A | 1/1996 | Kemp |
| 5,504,052 A | 4/1996 | Rizkalla et al. |
| 5,545,603 A | 8/1996 | Kemp |
| 5,663,385 A | 9/1997 | Kemp |
| 5,739,075 A | 4/1998 | Matusz |
| 5,801,259 A | 9/1998 | Kowaleski |
| 5,905,053 A * | 5/1999 | Rizkalla et al. ............. 502/216 |
| 5,929,259 A | 7/1999 | Lockemeyer |
| 6,103,916 A | 8/2000 | Takada et al. |
| 6,368,998 B1 | 4/2002 | Lockemeyer |
| 6,372,925 B1 | 4/2002 | Evans et al. |
| 6,579,825 B2 * | 6/2003 | Lockemeyer ............... 502/347 |
| 2002/0107410 A1 * | 8/2002 | Rizkalla et al. ............. 549/534 |

FOREIGN PATENT DOCUMENTS

| | | |
|---|---|---|
| EP | 0266015 | 10/1987 |
| EP | 07 16884 | 12/1995 |
| GB | 1571123 | 2/1976 |
| JP | 56/105750 | 8/1981 |

* cited by examiner

*Primary Examiner*—Elizabeth D. Wood
(74) *Attorney, Agent, or Firm*—William C. Long; Roberts & Roberts, LLP

(57) ABSTRACT

An ethylene oxide catalyst is provided which is essentially transition metal and rhenium free and which consists essentially of silver, alkali metal, sulfur and boron components on a support such as alumina, optionally with a fluorine or chlorine component.

4 Claims, No Drawings

ETHYLENE OXIDE CATALYST

BACKGROUND OF THE INVENTION

1. Field of the Invention

The present invention relates to a catalyst for the oxidation of ethylene to ethylene oxide consisting of a critical combination of silver, alkali metal such as cesium, boron and sulfur deposited on a support such as alpha alumina and to the production of ethylene oxide using the catalyst; a fluorine or chloride component optionally can be included. The catalyst is essentially free of rhenium or transition metal components.

2. Description of the Prior Art

Processes for the production of ethylene oxide involve the vapor phase oxidation of ethylene with molecular oxygen using a solid catalyst comprised of silver on a support such as alumina. There have been efforts by many workers to improve the effectiveness and efficiency of the silver catalyst for producing ethylene oxide. U.S. Pat. No. 5,051,395 provides a comprehensive analysis of these efforts of prior workers.

Among the many prior teachings in this area is that of U.S. Pat. No. 4,007,135 (see also UK 1,491,447) which teaches variously silver catalysts for the production of ethylene and propylene oxides comprised of a promoting amount of copper, gold, magnesium, zinc, cadmium, mercury, strontium, calcium, niobium, tantalum, molybdenum, tungsten, chromium, vanadium, and/or preferably barium, in excess of any present in immobile form in the performed support as impurities or cements (column 2, lines 1–15), silver catalysts for the production of propylene oxide comprising a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium, in excess of any present in immobile form in the preformed support as impurities or cements (column 2, lines 16–34), as well as silver catalysts for producing ethylene oxide or propylene oxide comprising (a) a promoting amount of sodium, cesium, rubidium, and/or potassium, and (b) magnesium, strontium, calcium and/or preferably barium in a promoting amount (column 3, lines 5–8).

U.S. Pat. No. 5,057,481, and related U.S. Pat. No. 4,908,343 are concerned with silver ethylene oxide catalysts comprised of cesium and an oxyanion of a group 3b to 7b element.

U.S. Pat. No. 3,888,889 describes catalysts suitable for the oxidation of propylene to propylene oxide comprised of elemental silver modified by a compound of an element from Group 5b and 6b. Although the use of supports is mentioned, there are no examples. The use of cesium is not mentioned.

European Publication 0 266 015 deals with supported silver catalysts promoted with rhenium and a long list of possible copromoters.

U.S. Pat. No. 5,102,848 deals with catalysts suitable for the production of ethylene oxide comprising a silver impregnated support also having thereon at least one cation promoter such as cesium, and a promoter comprising (i) sulfate anion, (ii) fluoride anion, and (iii) oxyanion of an element of Group 3b to 6b inclusive of the Periodic Table. Possibly for purposes of comparison since it is outside the scope of catalyst claimed, the patent shows at columns 21 and 22 a catalyst No. 6 comprised of Ag/Cs/S/F on a support.

U.S. Pat. No. 5,486,628 describes a silver catalyst promoted with alkali metal, rhenium and a rare earth or lanthanide component.

U.S. Pat. No. 5,011,807 is concerned with an ethylene oxide catalyst comprised of silver, alkali metal, a transition metal, and sulfur on alumina support. The support of choice in the preparation of commercial silver ethylene oxide catalysts has been a solid inorganic material such as alumina and silica, or titania based compounds, or combinations thereof. Alpha alumina, which may contain silica, has been an especially preferred carrier. Various patents have focused on the pretreatment of such carriers to improve the utility thereof U.S. Pat. No. 5,102,648, for example, shows repeated alpha alumina support washing with 90° C. de-ionized water prior to deposition of the catalyst components. In the same patent, the carrier was also washed with HF solution at 25° C. Later U.S. Pat. No. 6,103,916 similarly shows washing alpha alumina support with 90° C. water repeatedly prior to deposition of the catalytic components in ethylene oxide catalyst preparation.

The prior art has also disclosed that the catalyst's performance is improved with the addition of, specifically, thallium borate, JP-57-21937 (laid open on Feb. 4, 1982). Also, JP-56-105750 (laid open on Aug. 22, 1981) disclosed that the catalyst improvement is attained by adding boron along with Mo or W. In both cases, JP-57-21937 and 56-105750, the disclosures claimed that the carrier should not have more than 0.07% Na. This is in contrast with G.B. Patent 1,571, 123 (1980), which has disclosed the advantage of adding both sodium and boron to the silver-ethylene oxide catalyst.

In another group of patents, boron was disclosed as a Re co-promoter. In this group it was clearly stated " . . . it is preferable that if the catalyst contains rhenium, the catalyst also contains a rhenium co-promoter. When a co-promoter is utilized, it is selected from the group consisting of sulphur, molybdenum, tungsten, chromium, phosphorous, boron, and mixtures thereof". Examples of this group of patents are: U.S. Pat. No. 5,545,603, U.S. Pat. No. 5,663,385, U.S. Pat. No. 5,739,075, U.S. Pat. No. 5,801,259, U.S. Pat. No. 5,929,259, U.S. Pat. No. 6,372,925, U.S. Pat. No. 6,368,998, EP 0 900 128B1, EP 0 874 688B1m EP 0716884B1, PCT/EP97/01622, and PCT/EP97/02236.

In the process of preparing the alpha-alumina carrier, it is customary to add boric acid, or its salts, as a flux agent, to the powdered alumina. This is clearly illustrated by W. Wingery, et al in, Introduction to Ceramics, 2ed edition, 1976 P 8. and M. Bengisu in Engineering Ceramics, 2001, P 157. Addition of boric acid, or its salts, to the powdered alumina before firing the carrier was also disclosed in U.S. Pat. Nos. 5,100,824, 5,145,824, 5,384,302, and WO 97/40933.

In the context of the bewildering and vast number of references, many of them contradictory, applicant has discovered a novel and improved catalyst for the production of ethylene oxide.

BRIEF DESCRIPTION OF THE INVENTION

The present invention relates to an improved supported silver ethylene oxide catalyst containing a promoter combination consisting of an alkali metal component, preferably cesium, together with a sulfur component and a boron component, and to the catalyst preparation and use; the catalyst is essentially free of rhenium and transition metal components and optionally can contain a fluorine or chloride component.

DETAILED DESCRIPTION

We have discovered that the catalyst performance for ethylene oxide production is greatly enhanced when promoting levels of both boron and sulfur are co-precipitated on the carrier's surface with the precipitation of the silver metal and an alkali metal salt. The new invention does not require and, in fact precludes the presence of any of the added promoters TI, Mo, W or Re which were disclosed in the prior art.

In the instant invention, boron may be added to the impregnating solution in any soluble form e.g. boric acid, ammonium borate, potassium borate, cesium borate, and the like. The sulfur component can be added to the impregnating solution as sulfate, e.g. cesium sulfate, ammonium sulfate, and the like. U.S. Pat. No. 4,766,105 describes the use of sulfur promoting agents, for example at column 10, lines 53–60, and this disclosure is incorporated herein by reference. The amount of sulfur (expressed as the element) is preferred to be in the range of 5–300 ppm by weight, based on the weight of catalyst. Other sulfur compounds that may be used are cesium sulfate, potassium sulfate, ammonium sulfide, or sulfonic acids. These examples of boron and sulfur compounds are not limiting and were mentioned only for illustration.

The boron and/or S compounds may also be added to the catalyst in a separate step. This may be achieved in a pre- or post-impregnation step by dissolving the boron and/or sulfur compounds in a suitable solvent followed by catalyst impregnation using standard techniques, as will be illustrated in the examples section. Addition of boron and/or sulfur compounds in a post-impregnation step may affect the amount of alkali metal that was, optionally, deposited in an earlier impregnation. Therefore, it is essential that the post-impregnation solution will also have at least part of the alkali metal salt that is needed on the surface of the catalyst.

In most cases boron is present on the carrier's surface, and the near subsurface. Boron is a common flux agent that is mixed with the powdered alumina, and silica, in the carrier's preparation step. This boron is present on the carrier's surface, and in the near subsurface, it is incapable of providing the desired improvement in the catalytic performance, because most of it forms stable compounds with the surface silica and alumina.

The amount of the boron component is 5 to 500 ppm based on the weight of the catalyst, preferably 20 to 100 ppm expressed as boron. The amount of the alkali metal promoter is not more than 3000 ppm expressed as alkali metal based on the catalyst weight; preferably the catalyst contains 400–1500 ppm, more preferably 500–1200 ppm alkali metal based on the catalyst weight. Preferably the alkali metal is cesium although lithium, potassium, rubidium and mixtures of two or more alkali metals can also be used.

The catalyst may also contain a fluorine promoter in the amount expressed as the element of 10–300 ppm by weight based on the weight of the catalyst. Ammonium fluoride, alkali metal fluoride, and the like can be used.

Preferred catalysts prepared in accordance with this invention contain up to about 30% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–20% based on weight of total catalyst are preferred, while silver contents of 8–15% are especially preferred.

The catalysts are made with supports comprising alumina, silica, silica-alumina or combinations thereof. Preferred supports are those containing principally alpha-alumina, particularly those containing up to about 15 wt % silica. Especially preferred supports have a porosity of about 0.1–1.0 cc/g and preferably about 0.2–0.7 cc/g. Preferred supports also have a relatively low surface area, i.e. about 0.2–2.0 $m^2$/g, preferably 0.4–1.6 $m^2$/g and most preferably 0.5–1.3 $m^2$/g as determined by the BET method. See J. Am. Chem. Soc. 60, 3098–16 (1938). Porosities are determined by the mercury porosimeter method; see Drake and Ritter, "Ind. Eng. Chem. anal. Ed.," 17, 787 (1945). Pore and pore diameter distributions are determined from the surface area and apparent porosity measurements.

For use in commercial ethylene oxide production applications, the supports are desirably formed into regularly shaped pellets, spheres, rings, etc. Desirably, the support particles may have "equivalent diameters" in the range from 3–10 mm and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

Preferably, the silver is added to the support by immersion of the support into a silver impregnating solution or by the incipient wetness technique. The silver containing liquid penetrates by absorption, capillary action and/or vacuum into the pores of the support. A single impregnation or a series of impregnations, with or without intermediate drying, may be used, depending in part upon the concentration of the silver salt in the solution. To obtain catalyst having silver contents within the preferred range, suitable impregnating solutions will generally contain from 5–50 wt % silver, expressed as metal. The exact concentrations employed, of course, will depend upon, among other factors, the desired silver content, the nature of the support, the viscosity of the liquid, and solubility of the silver compound.

The impregnating solution, as already indicated, is characterized as a silver/amine solution, preferably such as is fully described in U.S. Pat. No. 3,702,259 the disclosure of which is incorporated herein by reference. The impregnation procedures described in U.S. Pat. No. 3,962,136 are advantageously employed for the cesium component.

Known prior procedures of predeposition, co-deposition and postdeposition of the various promoters can be employed.

After impregnation, any excess impregnating solution is separated and the support impregnated with silver and the promoter or promoters is calcined or activated. In the most preferred practice of the invention, calcination is carried out as described in commonly assigned U.S. Pat. No. 5,504,052 granted Apr. 2, 1996 and copending application Ser. No. 08/587,281 filed Jan. 16, 1996, the disclosures of which are incorporated herein by reference. The calcination is accomplished by heating the impregnated support, preferably at a gradual rate, to a temperature in the range 120–500° C. for a time sufficient to convert the contained silver to silver metal and to decompose the organic materials and remove the same as volatiles.

The impregnated support is maintained under an inert atmosphere while it is above 300° C. during the entire procedure. While not wishing to be bound by theory, it is believed that at temperatures of 300° C. and higher oxygen is absorbed in substantial quantities into the bulk of the silver where it has an adverse effect on the catalyst characteristics. Inert atmospheres as employed in the invention are those which are essentially free of oxygen.

An alternative method of calcination is to heat the catalyst in a stream of air at a temperature not exceeding 300° C., preferably not exceeding 280° C.

Catalysts prepared in accordance with the invention have improved performance, especially stability, for the production of ethylene oxide by the vapor phase oxidation of ethylene with molecular oxygen. These usually involve reaction temperatures of about 150° C. to 400° C., usually about 200° C. to 300° C., and reaction pressures in the range of from 0.5 to 35 bar. Reactant feed mixtures contain 0.5 to 30% ethylene and 3 to 15% oxygen, with the balance comprising comparatively inert materials including such substances as nitrogen, carbon dioxide, methane, ethane, argon and the like. Only a portion of the ethylene usually is reacted per pass over the catalyst and after separation of the desired ethylene oxide product and the removal of appropriate purge streams and carbon dioxide to prevent uncontrolled build up of inerts and/or by-products, unreacted materials are returned to the oxidation reactor.

The following examples illustrate the invention.

EXAMPLE 1

The carrier used is a low surface area alumina carrier, 0.9 $m^2/g$ surface area and has water absorption of 31.2 cc/100 g.

Carrier Pre-Treatment

Step 1. The treatment solution ($NH_4OH$ solution in water) was adjusted to the have a pH of 11.0 by the addition of the required amount of ammonium hydroxide. A 500 g sample of the carrier was placed in a pressure vessel and then exposed to vacuum until the pressure was reduced to 50 mm Hg. 1500 ml of the treatment solution was introduced to the flask while still under vacuum. When all the solution was added, the pressure of the vessel was allowed to rise to atmospheric pressure. The carrier and the liquid were then transferred to a jacketed addition funnel and the solution was allowed to circulate through the carrier's bed. The solution flowed constantly to the top of the funnel at a rate of about 5 L per hour. It was also drained, at the same rate, from the bottom of the funnel and the level of solution inside the funnel was maintained at about one inch above the level of the carrier. A hot liquid was allowed to circulate through the jacket to keep its temperature at 65° C.

Step 2. After 30 minutes the solution was drained, weighed and saved for analysis. 1500 ml of a fresh batch of the treatment solution was added and the procedure was repeated for additional 30 minutes. This step was repeated for a total of five cycles of washing.

Step 3. After the last cycle the carrier was washed with 1500 ml water at room temperature for 30 minutes.

Step 4. The water washing was repeated once and followed by draining the liquid and drying the carrier at 150° C. for 5 hours.

Stock Solution Preparation

Preparation of a Stock Solution of Silver/Amine Complex:

A silver solution was prepared using the following components
(parts are by weight):
Silver oxide—834 parts
Oxalic acid—444 parts
Ethylene diamine—566 parts Silver oxide was mixed with water, at room temperature, followed by the gradual addition of the oxalic acid. The mixture was stirred for 15 minutes and at that point, the color of the black suspension of silver oxide had changed to the gray/brown color of silver oxalate. The mixture was filtered and the solids were washed with 3 liters of de-ionized water. The sample was placed in an ice bath and stirred while ethylenediamine and water (as a 66%/34% mixture) were added slowly in order to maintain the reaction temperature lower than 33° C. After the addition of all the ethylenediamine/water mixture, the solution was filtered at room temperature. The clear filtrate was utilized as a silver/amine stock solution for the catalyst preparation.

Catalyst Preparation and Testing a. Promoters Addition:

The clear silver stock solution obtained above was diluted with a 66/34 mixture of ethylenediamine/water. In addition, Cs hydroxide, ammonium sulfate and boric acid were added to the solution in order to prepare a catalyst containing 11.5% silver, 90 ppm sulfur, 1200 ppm cesium and 100 ppm boron.

b. Catalyst Impregnation:

A 150 g sample of the carrier was placed in a pressure vessel and then exposed to vacuum until the pressure was reduced to 50 mm Hg. 200 ml of the adjusted silver/promoters solution was introduced to the flask while it is still under vacuum. The pressure of the vessel was allowed to rise to atmospheric pressure and its contents were shaken for few minutes. The catalyst was separated from the solution and was now ready for calcination.

c. Catalyst Calcination:

Calcination, deposition of silver, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. It was increased, up to 400° C., as the catalyst passed through seven heating zones. After the heating zones, the belt passed through a cooling zone that gradually cooled the catalyst to a temperature lower than 100° C.

The total residence time in the furnace was 22 minutes. The atmosphere of the furnace was controlled through the use of nitrogen flow in the different heating zone.

d. Catalyst Testing:

The catalyst was tested in a stainless steel tube that was heated by a molten salt bath. A gas mixture containing 15% ethylene, 7% oxygen, and 78% inert, mainly nitrogen and carbon dioxide, was passed through the catalyst at 300 psig. The temperature of the reaction was initially adjusted in order to obtain ethylene oxide productivity of 160 kg per hour per $m^3$ of catalyst.

COMPARATIVE EXAMPLE 2

Example 1 was repeated with the exception that no sulfur compound was added.

COMPARATIVE EXAMPLE 3

Example 1 was repeated with the exception that no boron compound was added.

The results of testing these catalysts are summarized in Table 1.

TABLE 1

| | Promoters, amounts in ppm | | | |
|---|---|---|---|---|
| Example | S | Cs | B | Selectivity |
| 1 | 90 | 1200 | 100 | 84.6 |
| Comparative Example 2 | 0 | 1200 | 100 | 67 |
| Comparative Example 3 | 90 | 1200 | 0 | 81.9 |

From the results shown in Table 1, it can be seen that the catalyst of the invention gives outstanding results in the production of ethylene oxide in the absence of rhenium or transition metal additives. By way of contrast, when either the boron or sulfur component is not employed sustantially inferior results are achieved.

EXAMPLES 4–6

A second series of catalysts was prepared and tested using the general procedure described in example 1. In this series, the carrier pretreatment involved using lithium hydroxide solution that was adjusted at pH value of 12.5. This pH value was maintained through out the pretreatment procedure by adding small amount of LiOH solution when needed.

The promoters added to the silver impregnating solution were Cs hydroxide, Cs sulfate, and potassium borate. These promoters were added in amounts sufficient to give catalysts comprising the compositions indicated in table 2:

TABLE 2

| | | Promoters, amounts in ppm | | | |
| --- | --- | --- | --- | --- | --- |
| Example | Ag % | S | Cs | B | Selectivity |
| 4 | 11.9 | 90 | 800 | 50 | 86.1 |
| 5 | 11.85 | 0 | 800 | 50 | 81.7 |
| 6 | 11.9 | 90 | 800 | 0 | 84.1 |

EXAMPLE 7

In this example, the carrier pretreatment involved using 0.015N ammonium fluoride solution at 85° C. The promoters added to the silver impregnating solution were Cs hydroxide, Cs sulfate, and ammonium borate. These promoters were added in amounts sufficient to give catalysts comprising 12% silver, 800 ppm Cs, and 80 ppm S. Testing this catalyst, as described in example-1, gave a selectivity of 84.9%.

What is claimed is:

1. A rhenium and transition metal free catalyst for the oxidation of ethylene to ethylene oxide comprised of silver on a solid support and containing a promoter combination consisting essentially of (1) 400–1500 ppm based on the weight of the catalyst of an alkali metal component, (2) 5–500 ppm based on the weight of the catalyst of a boron component, and (3) 5–300 ppm based on the weight of the catalyst of a sulfur component.

2. The catalyst of claim 1 wherein the alkali metal component is cesium.

3. The catalyst of claim 1 wherein the support is alpha alumina.

4. The catalyst of claim 1 comprised by weight of 5–20% silver.

* * * * *